United States Patent
Barritault et al.

(10) Patent No.: US 6,932,973 B2
(45) Date of Patent: Aug. 23, 2005

(54) PEPTIDES WHICH STIMULATE THE EXPRESSION OF THE CYTOKINES OF INFLAMMATION AND PROMOTE TISSUE REGENERATION

(75) Inventors: Denis Barritault, Paris (FR); Ammar Achour, Créteil (FR); Jose Courty, Villecresnes (FR)

(73) Assignee: Centre National de la Recherche Scientifique—CNRS (FR)

( * ) Notice: Subject to any disclaimer, the term of this patent is extended or adjusted under 35 U.S.C. 154(b) by 0 days.

(21) Appl. No.: 10/116,391

(22) Filed: Apr. 4, 2002

(65) Prior Publication Data

US 2003/0087255 A1 May 8, 2003

Related U.S. Application Data

(63) Continuation of application No. PCT/FR00/02786, filed on Oct. 6, 2000.

(30) Foreign Application Priority Data

Oct. 12, 1999 (FR) ............................................ 99 12714

(51) Int. Cl.[7] ............................................ A61K 45/00
(52) U.S. Cl. .................................................. 424/278.1
(58) Field of Search ................................ 530/324–328; 424/278.1

(56) References Cited

U.S. PATENT DOCUMENTS 5,736,294 A  4/1998  Ecker et al.
5,932,218 A  *  8/1999  Berzofsky et al. ....... 424/188.1
6,103,880 A  *  8/2000  Barritault et al. ........... 530/399

OTHER PUBLICATIONS

Horst Ibelgaufts' COPE Cytokine Online Pathfinder Encyclopaedia http://www.copewithcytokines.de/cope.cgi?002632.*

Frédéric Jonca et al., *Cell Release of Bioactive Fibroblast Growth Factor 2 by Exon 6–encoded Sequence of Vascular Endothelial Growth Factor*, The Journal of Biological Chemistry, vol. 272, No. 39, Sep. 26, 1997, pp. 24203–24209.

* cited by examiner

*Primary Examiner*—Jeffrey Stucker
(74) *Attorney, Agent, or Firm*—DLA Piper Rudnick Gray Cary US LLP

(57) ABSTRACT

A pharmaceutical composition for stimulating production of cytokines of inflammation including a peptide corresponding to formula (I) below:

$$(A)_n\text{-}A1\text{-}A1\text{-}A2\text{-}A1\text{-}A3\text{-}A4\text{-}A1\text{-}(A)_m$$

in which A is any amino acid, n and m are each whole numbers from 0 to 20 whose sum n+m is between 0 and 20, A1 is a basic amino acid and more particularly lysine (Lys) or arginine (Arg), A2 is an amino acid selected from the group consisting of basic amino acids, glutamic acid (Glu), glycine (Gly) and aspartic acid (Asp), A3 is an amino acid selected from the group consisting of basic amino acids, proline (Pro), glutamic acid (Glu) and glutamine (Gln), A4 is an amino acid selected from the group consisting of basic amino acids, glutamic acid (Glu), glycine (Gly), serine (Ser) and valine (Val), and a pharmaceutically acceptable carrier.

2 Claims, 7 Drawing Sheets

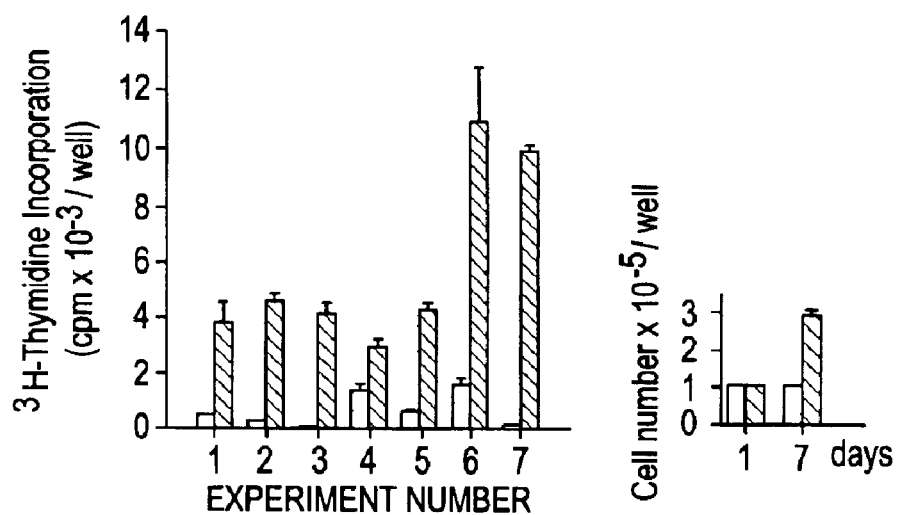
FIG. 1
FIG. 2A
FIG. 2B
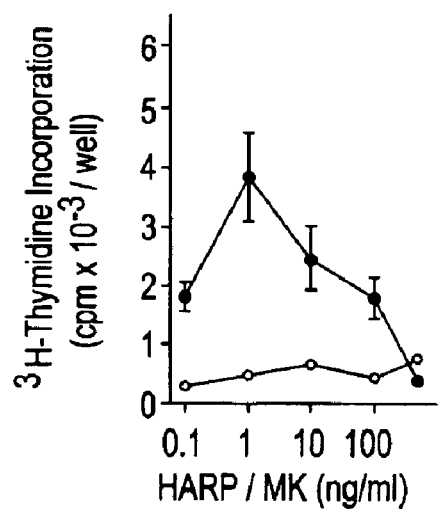
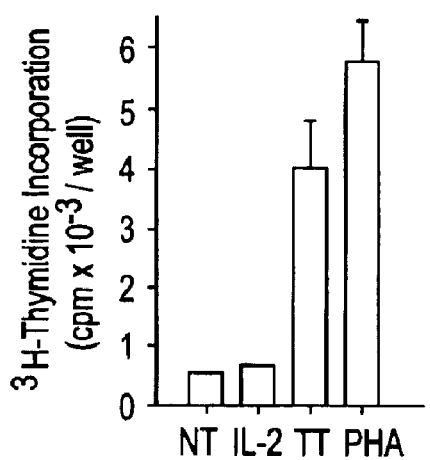

Effect of HARP on the proliferation of PBMCs treated with an anti-CD3

Effect of HARP on the proliferatiion of PBMCs treated with tetanus toxin

Effect of HARP on the proliferatiion of HIV

Effect of HARP peptides on the proliferation of PBMCs

Quantitative determination
IL-1 HARP / PBMC

Quantitative determination
TNF HARP / PBMC

Quantitative determination
IL-6 HARP / PBMC

Induction of IL-6 on PBMCs

SEQUENCE LISTING

```
<160> NUMBER OF SEQ ID NOS: 23

<210> SEQ ID NO 1
<211> LENGTH: 14
<212> TYPE: PRT
<213> ORGANISM: Unknown Organism
<220> FEATURE:
<223> OTHER INFORMATION: Description of Unknown Organism: HARP
      peptide fragment

<400> SEQUENCE: 1

Gly Lys Lys Glu Lys Pro Glu Lys Lys Val Lys Lys Ser Asp
  1               5                  10

<210> SEQ ID NO 2
<211> LENGTH: 23
<212> TYPE: PRT
<213> ORGANISM: Human immunodeficiency virus type 2

<400> SEQUENCE: 2

Lys Gly Leu Gly Ile Cys Tyr Glu Arg Lys Gly Arg Arg Arg Arg Thr
  1               5                  10                  15

Pro Lys Lys Thr Lys Thr His
                 20

<210> SEQ ID NO 3
<211> LENGTH: 30
<212> TYPE: PRT
<213> ORGANISM: Unknown Organism
<220> FEATURE:
<223> OTHER INFORMATION: Description of Unknown Organism: HB-EGF
      peptide fragment

<400> SEQUENCE: 3

Ala Thr Pro Asn Lys Glu Glu His Gly Lys Arg Lys Lys Lys Gly Lys
  1               5                  10                  15

Gly Leu Gly Lys Lys Arg Asp Pro Cys Leu Arg Lys Tyr Lys
                 20                  25                  30

<210> SEQ ID NO 4
<211> LENGTH: 25
<212> TYPE: PRT
<213> ORGANISM: Unknown Organism
<220> FEATURE:
<223> OTHER INFORMATION: Description of Unknown Organism: HARP
      peptide fragment

<400> SEQUENCE: 4

Lys Leu Thr Lys Pro Lys Pro Gln Ala Glu Ser Lys Lys Lys Lys Lys
  1               5                  10                  15

Glu Gly Lys Lys Gln Glu Lys Met Leu
                 20                  25
```

```
<210> SEQ ID NO 5
<211> LENGTH: 29
<212> TYPE: PRT
<213> ORGANISM: Unknown Organism
<220> FEATURE:
<223> OTHER INFORMATION: Description of Unknown Organism: FGF-2
      peptide fragment

<400> SEQUENCE: 5

Arg Ser Arg Lys Tyr Thr Ser Trp Tyr Val Ala Leu Lys Arg Thr Gly
  1               5                  10                  15

Gln Tyr Lys Leu Gly Ser Lys Thr Gly Pro Gly Gln Pro
             20                  25

<210> SEQ ID NO 6
<211> LENGTH: 25
<212> TYPE: PRT
<213> ORGANISM: Unknown Organism
<220> FEATURE:
<223> OTHER INFORMATION: Description of Unknown Organism: HGF
      peptide fragment

<400> SEQUENCE: 6

Ile Ala Ile Pro Tyr Ala Glu Gly Arg Lys Arg Arg Asn Thr Ile His
  1               5                  10                  15

Glu Phe Lys Lys Ser Ala Lys Thr Thr
             20                  25

<210> SEQ ID NO 7
<211> LENGTH: 25
<212> TYPE: PRT
<213> ORGANISM: Unknown Organism
<220> FEATURE:
<223> OTHER INFORMATION: Description of Unknown Organism: VEGF
      peptide fragment

<400> SEQUENCE: 7

Arg Gly Lys Gly Lys Gly Pro Lys Arg Lys Arg Lys Lys Ser Arg Tyr
  1               5                  10                  15

Lys Ser Trp Ser Val Pro Cys Gly Pro
             20                  25

<210> SEQ ID NO 8
<211> LENGTH: 25
<212> TYPE: PRT
<213> ORGANISM: Human immunodeficiency virus type 1

<400> SEQUENCE: 8

Lys Gly Leu Gly Ile Ser Tyr Gly Arg Lys Lys Arg Arg Gln Arg Arg
  1               5                  10                  15

Arg Pro Pro Gln Gly Asn Gln Ala His
             20                  25

<210> SEQ ID NO 9
<211> LENGTH: 16
<212> TYPE: PRT
<213> ORGANISM: Unknown Organism
<220> FEATURE:
<223> OTHER INFORMATION: Description of Unknown Organism: MK
      peptide fragment

<400> SEQUENCE: 9

Pro Lys Thr Lys Ala Lys Ala Lys Ala Lys Lys Gly Lys Gly Lys Asp
  1               5                  10                  15
```

```
<210> SEQ ID NO 10
<211> LENGTH: 11
<212> TYPE: PRT
<213> ORGANISM: Unknown Organism
<220> FEATURE:
<223> OTHER INFORMATION: Description of Unknown Organism: MK
      peptide fragment

<400> SEQUENCE: 10

Lys Lys Lys Asp Lys Val Lys Lys Gly Gly Pro
 1               5                  10

<210> SEQ ID NO 11
<211> LENGTH: 24
<212> TYPE: PRT
<213> ORGANISM: Unknown Organism
<220> FEATURE:
<223> OTHER INFORMATION: Description of Unknown Organism:
      Angiogenin peptide fragment

<400> SEQUENCE: 11

Arg Tyr Cys Glu Ser Ile Met Arg Arg Gly Leu Thr Ser Pro Cys
 1               5                  10                  15

Lys Asp Ile Asn Thr Phe Ile Asn
            20

<210> SEQ ID NO 12
<211> LENGTH: 28
<212> TYPE: PRT
<213> ORGANISM: Unknown Organism
<220> FEATURE:
<223> OTHER INFORMATION: Description of Unknown Organism:
      FGF-1 peptide fragment

<400> SEQUENCE: 12

Lys Phe Asn Leu Pro Pro Gly Asn Tyr Lys Lys Pro Lys Leu Leu Tyr
 1               5                  10                  15

Cys Ser Asn Gly Gly His Phe Leu Arg Ile Leu Pro
            20                  25

<210> SEQ ID NO 13
<211> LENGTH: 29
<212> TYPE: PRT
<213> ORGANISM: Unknown Organism
<220> FEATURE:
<223> OTHER INFORMATION: Description of Unknown Organism:
      FGF-1 peptide fragment

<400> SEQUENCE: 13

Lys Lys His Ala Glu Lys Asn Trp Phe Val Gly Leu Lys Lys Asn Gly
 1               5                  10                  15

Ser Cys Lys Arg Gly Pro Arg Thr His Tyr Gly Tyr Lys
            20                  25

<210> SEQ ID NO 14
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions
      described in the specification as filed
<220> FEATURE:
```

```
<221> NAME/KEY: VARIANT
<222> LOCATION: (28)..(47)
<223> OTHER INFORMATION: Xaa = any amino acid; this range may
      encompass 0-20 residues according to the provisions
      described in the specification as filed

<400> SEQUENCE: 14

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Lys Lys Glu Lys Pro Glu Lys Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 15
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions described
      in the specification as filed
<220> FEATURE:
<221> NAME/KEY: VARIANT
<222> LOCATION: (28)..(47)
<223> OTHER INFORMATION: Xaa = any amino acid; this range may
      encompass 0-20 residues according to the provisions described
      in the specification as filed

<400> SEQUENCE: 15

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Arg Lys Gly Arg Arg Arg Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 16
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions
      described in the specification as filed
<220> FEATURE:
<221> NAME/KEY: VARIANT
<222> LOCATION: (28)..(47)
<223> OTHER INFORMATION: Xaa = any amino acid; this range may
      encompass 0-20 residues according to the provisions described
      in the specification as filed

<400> SEQUENCE: 16

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Lys Arg Lys Lys Lys Gly Lys Xaa Xaa Xaa Xaa
             20                  25                  30

Xaa Xaa Xaa Xaa Xaa Xaa Xaa Xaa Xaa Xaa Xaa Xaa Xaa Xaa Xaa
```

```
          35                  40                  45

<210> SEQ ID NO 17
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions
      described in the specification as filed
<220> FEATURE:
<221> NAME/KEY: VARIANT
<222> LOCATION: (28)..(47)
<223> OTHER INFORMATION: Xaa = any amino acid; this range may
      encompass 0-20 residues according to the provisions described
      in the specification as filed

<400> SEQUENCE: 17

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Lys Lys Lys Lys Glu Gly Lys Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 18
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions
      described in the specification as filed
<220> FEATURE:
<221> NAME/KEY: VARIANT
<222> LOCATION: (28)..(47)
<223> OTHER INFORMATION: Xaa = any amino acid; this range may
      encompass 0-20 residues according to the provisions described
      in the specification as filed

<400> SEQUENCE: 18

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Arg Lys Arg Lys Lys Ser Arg Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 19
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions
```

```
        described in the specification as filed
<220> FEATURE:
<221> NAME/KEY: VARIANT
<222> LOCATION: (28)..(47)
<223> OTHER INFORMATION: Xaa = any amino acid; this range may
        encompass 0-20 residues according to the provisions described
        in the specification as filed

<400> SEQUENCE: 19

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Lys Lys Arg Arg Gln Arg Arg Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 20
<211> LENGTH: 47
<212> TYPE: PRT
<213> ORGANISM: Artificial Sequence
<220> FEATURE:
<223> OTHER INFORMATION: Description of Artificial Sequence:
        Formula sequence
<220> FEATURE:
<221> NAME/KEY: VARIANT
<222> LOCATION: (1)..(20)
<223> OTHER INFORMATION: Xaa = any amino acid; this range may
        encompass 0-20 residues according to the provisions described
        in the specification as filed
<220> FEATURE:
<221> NAME/KEY: VARIANT
<222> LOCATION: (28)..(47)
<223> OTHER INFORMATION: Xaa = any amino acid; this range may
        encompass 0-20 residues according to the provisions described
        in the specification as filed

<400> SEQUENCE: 20

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Lys Lys Asp Lys Val Lys Lys Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 21
<211> LENGTH: 21
<212> TYPE: PRT
<213> ORGANISM: Unknown Organism
<220> FEATURE:
<223> OTHER INFORMATION: Description of Unknown Organism: HARP
        peptide fragment

<400> SEQUENCE: 21

Ala Glu Ala Gly Lys Lys Glu Lys Pro Glu Lys Lys Val Lys Lys Ser
  1               5                  10                  15

Asp Cys Gly Glu Trp
             20

<210> SEQ ID NO 22
<211> LENGTH: 18
<212> TYPE: PRT
<213> ORGANISM: Unknown Organism
<220> FEATURE:
<223> OTHER INFORMATION: Description of Unknown Organism: HARP
        peptide fragment

<400> SEQUENCE: 22
```

```
Ala Glu Ser Lys Lys Lys Lys Glu Gly Lys Lys Gln Glu Lys Met
 1               5                  10                  15
Leu Asp

<210> SEQ ID NO 23
<211> LENGTH: 47
<212> TYPE: PRT
<213> ORGANISM: Artificial Sequence
<220> FEATURE:
<223> OTHER INFORMATION: Description of Artificial Sequence:
      Formula sequence
<220> FEATURE:
<221> NAME/KEY: VARIANT
<222> LOCATION: (1)..(20)
<223> OTHER INFORMATION: Xaa = any amino acid; this range may
      encompass 0-20 residues according to the provisions described
      in the specification as filed
<220> FEATURE:
<221> NAME/KEY: VARIANT
<222> LOCATION: (21)..(22)
<223> OTHER INFORMATION: Xaa = Lys or Arg
<220> FEATURE:
<221> NAME/KEY: VARIANT
<222> LOCATION: (23)
<223> OTHER INFORMATION: Xaa = Glu, Gly or Asp
<220> FEATURE:
<221> NAME/KEY: VARIANT
<222> LOCATION: (24)
<223> OTHER INFORMATION: Xaa = Lys or Arg
<220> FEATURE:
<221> NAME/KEY: VARIANT
<222> LOCATION: (25)
<223> OTHER INFORMATION: Xaa = Pro, Glu or Gln
<220> FEATURE:
<221> NAME/KEY: VARIANT
<222> LOCATION: (26)
<223> OTHER INFORMATION: Xaa = Glu, Gly, Ser or Val
<220> FEATURE:
<221> NAME/KEY: VARIANT
<222> LOCATION: (28)..(47)
<223> OTHER INFORMATION: Xaa = any amino acid; this range may
      encompass 0-20 residues according to the provisions described
      in the specification as filed

<400> SEQUENCE: 23

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45
```

PEPTIDES WHICH STIMULATE THE EXPRESSION OF THE CYTOKINES OF INFLAMMATION AND PROMOTE TISSUE REGENERATION

RELATED APPLICATION

This is a continuation of International Application No. PCT/FR00/02786, with an international filing date of Oct. 6, 2000, which is based on French Patent Application No. 99/12714, filed Oct. 12, 1999.

FIELD OF THE INVENTION

This invention concerns a new family of peptide molecules having the capacity especially of stimulating the expression of the cytokines of inflammation and promoting regeneration of tissues. The invention, thus, also pertains to pharmaceutical compositions containing at least one of the peptides.

BACKGROUND

Known in the prior art are numerous angiogenic growth factors such as factors HARP, MK, FGF-1, FGF-2, VEGF, HIV1-tat, HIV2-tat, HGF, HB-EGF and angiogenin. Among these factors, HARP (Heparin Affin Regulatory Peptide), which is also called PTN (pleiotrophin) or HB-GAM (heparin binding-growth associated molecule), constitutes with MK (Midkine) a family of structurally related growth/differentiation factors that bind to heparin and having 50% homology in amino acids [1, 2].

The growth factor HARP is a polypeptide of 168 amino acids containing an N-terminal hydrophobic motif of 32 amino acids corresponding to a signal peptide. In its mature form, HARP is a secreted protein of 136 amino acids in its short form or 139 amino acids in its long form, whose apparent molecular weight, determined in SDS-PAGE under reducing conditions, is 18 kDa.

HARP was initially isolated from rat neonate brains as a molecule inducing in vitro neurite growth [3], suggesting that this polypeptide is involved in the maturation of neuronal cells [4]. Subsequent studies showed that this polypeptide was also present in non-neuronal tissues, such as the heart [5], uterus [6], cartilage [7] and bone extracts [8], demonstrating that the function of HARP is not limited to a promotional action on neurite growth as previously reported [3].

HARP is capable of stimulating the growth of fibroblastic, epithelial and endothelial cells in vitro [6, 9]. This mitogenic action has since been confirmed by the use of recombinant proteins produced from eukaryote expression systems [9, 12]. HARP also induces in vitro the formation of pseudocapillaries. In vivo, in different tissue models, localization of HARP is especially associated with endothelial cells of blood capillaries [16]. The data concerning HARP available at present suggest that this polypeptide plays a role in the complex mechanisms involved in angiogenesis and in tumor neoangiogenesis. Extensive research has been performed with regard to this aspect to determine the involvement of HARP in tumoral progression, particularly, in hormone-dependent tumors such as the breast and prostate.

Studies pertaining to the biological properties of HARP have been performed by numerous laboratories [2] and, despite much debated results, it appears that HARP, like MK, is involved in the control of cellular proliferation [2, 9–11]. Moreover, it has been demonstrated that human purified recombinant HARP proteins are mitogenic for endothelial cells [9, 12] and exert in vitro an angiogenic action [12]. Numerous studies have shown the involvement of HARP and MK in developmental processes [10, 13, 14]. Studies of the distribution of HARP protein mRNA during embryonic and postnatal development suggest important functions in cell growth and differentiation [15]. Nevertheless, the physiological functions in vivo of these molecules is still poorly understood. The presence of HARP transcripts in adult tissues including the meninges, iris, testicles and uterus also indicates a physiological role in adult age.

SUMMARY OF THE INVENTION

This invention relates to a pharmaceutical composition for stimulating production of cytokines of inflammation including a peptide corresponding to formula (I) below:

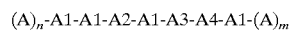

$(A)_n$-A1-A1-A2-A1-A3-A4-A1-$(A)_m$ in which A is any amino acid, n and m are each whole numbers from 0 to 20 whose sum n+m is between 0 and 20, A1 is a basic amino acid and more particularly lysine (Lys) or arginine (Arg), A2 is an amino acid selected from the group consisting of basic amino acids, glutamic acid (Glu), glycine (Gly) and aspartic acid (Asp), A3 is an amino acid selected from the group consisting of basic amino acids, proline (Pro), glutamic acid (Glu) and glutamine (Gln), A4 is an amino acid selected from the group consisting of basic amino acids, glutamic acid (Glu), glycine (Gly), serine (Ser) and valine (Val), and a pharmaceutically acceptable carrier.

BRIEF DESCRIPTION OF THE DRAWINGS

Other advantages and characteristics of the invention will become manifest from the description below concerning Examples with reference to the attached drawings in which:

FIG. 1 shows the stimulation of the incorporation of tritiated thymidine in PBMCs which have been stimulated or not stimulated by HARP. Clear bar: unstimulated cells; hatched bar: cells stimulated by 100 ng/ml of HARP.

FIG. 2 shows the dose-response effect of HARP tested on PBMCs. A) The cells were cultured in the absence of or in the presence of different concentrations ranging from 0.1 to 100 ng/ml of HARP (●-●) or midkine (MK) (o-o). Each of the values represents the mean of the cpm obtained±the standard deviation. B) The cells were incubated with tetanus toxin (TT) at 1800 IU/ml, phytohemagglutinin (PHA) at 2.5 μg/ml, interleukin-2 (IL-2) at 50 IU/ml, or not treated (NT) as internal controls of stimulation.

FIG. 11 shows the effect of the HARP peptides on muscle regeneration. Adult rat soleus muscle was crushed and then treated or not treated by the peptides, and then collected after 4 days of regeneration.

FIG. 12 shows the angiogenic effect of peptide 1 tested in CAMs.

DETAILED DESCRIPTION

Figure 3:
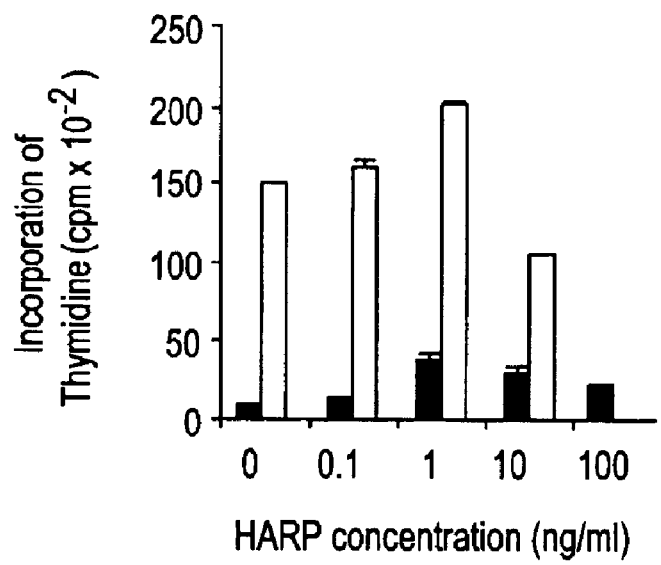
FIG. 3 shows the dose-response effect of HARP on PBMCs treated by an anti-CD3. The cells were cultured as described above. It should be noted that a high cell mortality was seen when the cells were treated with 100 ng/ml of HARP in the presence of CD3. Black bar: HARP alone; clear bar: HARP+anti-CD3.

Our investigative studies focused on numerous angiogenic growth factors such as FGF-1, FGF-2, VEGF, HIV1-tat, HIV2-tat, HB-EGF, angiogenin, HARP and MK. We were able to identify the peptide sequences contained in many of these factors. Based on these sequences, we constructed peptide molecules rich in the basic amino acids lysine (K) and arginine (R).

Table I below presents the portions of sequences rich in basic amino acids of various growth factors in which the positions of the basic amino acids are essentially aligned.

TABLE I

| Growth factor | Sequence |
|---|---|
| HARP (1–14) | GKKEKPEKKVKKSD (SEQ ID NO: 1) |
| HIV-2-tat (70–92) | K-GLGICYERKGRRRRTPKKTK-TH (SEQ ID NO: 2) |
| HB-EGF (85–114) | ATPNKEEHGKRKKKGKGLGKKRDPCLRKYK (SEQ ID NO: 3) |
| HARP (108–132) | KLTKPKPQAESKKKKKEGKKQEKML (SEQ ID NO: 4) |
| FGF-2 (116–141) | RSRKYTSWYVALKRTGQYKLGSKTGPGQP (SEQ ID NO: 5) |
| HGF (25–50) | IAIPYAEGORKRRNTIHEFKKSAKTT (SEQ ID NO: 6) |
| VEGF (145–170) | RGKGKGPKRKRKKSRYKSWSVPCGP (SEQ ID NO: 7) |
| HIV1-tat (41–65) | KGLGISYGRKKRRQRRRPPQGNQAH (SEQ ID NO: 8) |
| MK (106–122) | PKTKAKAKAKKGKG-KD (SEQ ID NO: 9) |
| MK (1–11) | KKKDKVKKGGP (SEQ ID NO: 10) |
| Angiogenin (24–50) | RYCESIMRRRGLTSPCKDINTFIN (SEQ ID NO: 11) |
| FGF-1 (15–42) | KFNLPPGNYKKPKLLYCSNGGHFLRILP (SEQ ID NO: 12) |
| FGF-1 (115–140) | KKHAEKNWFVGLKKNGSCKRGPRTHYGYK (SEQ ID NO: 13) |

Thus, the invention provides a peptide responding to formula (I) below:

$(A)_n$-A1-A1-A2-A1-A3-A4-A1-$(A)_m$ in which:

A is any amino acid;

n and m are each whole numbers from 0 to 20 whose sum n+m is between 0 and 20, preferably between 0 and 15, and especially preferably between 0 and 10;

A1 is a basic amino acid and more particularly lysine (Lys) or arginine (Arg);

A2 is an amino acid selected from among: the basic amino acids, glutamic acid (Glu), glycine (Gly), aspartic acid (Asp);

A3 is an amino acid selected from among: the basic amino acids, proline (Pro), glutamic acid (Glu), glutamine (Gln);

A4 is an amino acid selected from among: the basic amino acids, glutamic acid (Glu), glycine (Gly), serine (Ser), valine (Val).

The peptides of formula (I) according to the invention will also be designated "pAHA" to indicate "angiogenic peptide of HARP".

The invention envisages more particularly the peptides of the following formulas:

$(A)_n$-Lys-Lys-Glu-Lys-Pro-Glu-Lys-$(A)_m$ (SEQ ID NO: 14)    (II)

$(A)_n$-Arg-Lys-Gly-Arg-Arg-Arg-Arg-$(A)_m$ (SEQ ID NO: 15)    (III)

$(A)_n$-Lys-Arg-Lys-Lys-Lys-Gly-Lys-$(A)_m$ (SEQ ID NO: 16)    (IV)

$(A)_n$-Lys-Lys-Lys-Lys-Glu-Gly-Lys-$(A)_m$ (SEQ ID NO: 17)    (V)

$(A)_n$-Arg-Arg-Lys-Lys-Ser-Arg-$(A)_m$ (SEQ ID NO: 18)    (VI)

$(A)_n$-Lys-Lys-Atg-Arg-Gln-Arg-Arg-$(A)_m$ (SEQ ID NO: 19)    (VII)

$(A)_n$-Lys-Lys-Asp-Lys-Val-Lys-Lys-$(A)_m$ (SEQ ID NO: 20)    (VIII)

in which A, n and m have the same meaning as in formula (I).

The peptide of formula (II) was defined more particularly from the sequence of HARP (1–14).

The peptide of formula (III) was defined more particularly from the sequence of HIV-tat (70–92).

The peptide of formula (IV) was defined more particularly from the sequence of HB-EGF (85–114).

The peptide of formula (V) was defined more particularly from the sequence of HARP (108–132).

The peptide of formula (VI) was defined more particularly from the sequence of VEGF (145–170).

The peptide of formula (VII) was defined more particularly from the sequence of HIV-tat (41–65).

The peptide of formula (VIII) was defined more particularly from the sequence of MK (1–11).

The peptides of the invention can be prepared by chemical synthesis or by genetic expression techniques from the corresponding polynucleotide sequence by techniques known in the art.

We demonstrated that the pAHA peptides present angiogenic and cicatrizing properties like HARP and at comparable doses (ED50#5–50 ng/ml). In fact, we observed the remarkable action of these peptides on vascular ischemia (angiogenesis), muscle regeneration and cicatrization. We have also demonstrated that the peptides of the invention are capable of stimulating the expression of the cytokines of inflammation and are, thus, useful for preventing or treating diseases linked to immunodepression and, more particularly, AIDS.

The invention, thus, also pertains to a pharmaceutical composition containing one or more of the preceding peptides associated in said composition with one or more pharmaceutically acceptable vehicles.

Taking into account the properties of the peptides described above with regard to tissue regeneration, the invention concerns more particularly a composition comprising one or more pAHA peptides, and possibly another compound, that is useful for promoting cell regeneration and growth, such as muscle growth and cicatrization.

Due to the properties of the peptides described above with regard to angiogenesis, the invention concerns, more particularly, a composition comprising one or more pAHA peptides and possibly another compound that is useful for preventing or treating vascular ischemia.

As indicated above, our research studies made it possible to demonstrate the unexpected properties of the pAHA peptides on the proliferation of the circulating cells of the blood and, more particularly, on mononucleated cells of peripheral blood. A detailed study of this property demonstrated the stimulatory properties of pAHA on certain cytokines, more particularly, the cytokines of inflammation.

In fact, the presence of mRNA of the HARP protein has been observed in the cells of the blood vessels, both in the endothelial cells and the smooth muscle cells, as well as in human mammary glands [16]. Furthermore, it has been reported that HARP is an angiogenic growth factor [12] and that it is synthesized and localized in the vascular endothelial cells [16].

We, therefore, evaluated the action in vitro of this growth factor on freshly isolated PBMCs (human mononucleated cells of the peripheral blood) by incubating PBMCs with the HARP factor or with a pAHA peptide. The results showed that HARP and pAHA are capable of stimulating the incorporation of tritiated thymidine in the nuclei of PBMCs. These results, thus, demonstrate that the HARP molecule, as well as the pAHA peptide, strongly stimulate proliferation of human mononucleated cells of peripheral blood and, more particularly, after one week there is seen an augmentation in the population of T lymphocytes.

Our experiments showed that HARP is active on the proliferation of lymphocytes at very weak concentrations on the order of 10 pM. This surprising result led us to consider that the HARP factor must bind to its receptor on the PBMCs with a strong affinity.

After incubation of PBMCs with HARP factor, no increase in the IL-2 levels was seen. We, therefore, concluded that HARP does not act on the production of IL-2 interleukins, but that HARP and pAHA bind with strong affinity to a specific receptor present on the lymphocytes and induce the activation of the interleukin sites, most particularly, the IL-2 sites.

Our knowledge to date regarding the HARP receptors is incomplete. The presence of strong affinity HARP binding sites (Kd=600 pM) in NIH 3T3 cells has already been reported [20]. These HARP binding sites have also been found in various cell types, including rat kidney cells, human mammary adenocarcinoma cells, human epidermal carcinoma cells, human hepatocarcinoma cells, mouse neuroblasts and pheochromocytoma cells.

It is commonly accepted that no biological response transmitted by HARP was observed on this type of cell and that, consequently, these binding sites can not be considered to be functional receptors. Parallel studies describe the interactions between HARP and the heparan sulfate proteoglycans such as syndecan-1 and syndecan-2. It has been shown that syndecan-3 interacts with HARP with an apparent Kd of 800 pM. This heparan sulfate proteoglycan is involved in the neurite outgrowth action of HARP because the anti-syndecan-3 antibodies can block this activity [21].

More recently, a report by Maeda et al. described the binding of HARP with the binding sites of weak affinity (Kd=3 nM) and of strong affinity (Kd=250 pM) to phosphacan, an extracellular variant of a similar receptor, a β phosphatase tyrosine protein, RPTP β [22].

It is of interest to note that although MK (midkine) and HARP belong to the same family of molecules and both induce neurite outgrowth [17, 23], no induction of tritiated thymidine incorporation in the PBMCs was detected when using MK, which suggests that MK and HARP bind to different surface receptors, which, in fact, has recently been demonstrated [24, 25]. Moreover, the two molecules are expressed and isolated using similar experimental methods, including the same expression recombinant system and the same purification techniques. The fact that the incorporation of tritiated thymidine is seen solely with HARP and not with MK excludes the presence of a bacterial contaminant presenting a mitogenic activity in relation to PBMCs.

Depending on the donors of the PBMCs, different indices of stimulation have been seen. The most significant mitogenic effect induced by HARP is best observed by using quiescent cells, without activation of the PBMCs by lectins, like PHA recommended for the mitogenic activity induced by IL-2. This result clearly confirms the fact that HARP does not induce a stimulation of the production of IL-2.

The results obtained, thus, show that the pAHA peptide acts on the proliferation of immune cells and, more specifically, on the T lymphocytes. The invention consequently pertains, more particularly, to a pharmaceutical composition comprising one or more pAHA peptides, and possibly another compound, that is useful for stimulating the proliferation of mononucleated cells of blood and, more particularly, the T lymphocytes. The stimulation of the proliferation of the T lymphocyte cells is most particularly useful in the treatment of immunosuppressed patients.

Another observation was obtained on cells obtained from blood from AIDS patients. In Example 4 below, the inventors demonstrate how the stimulation of the cells from the patient's blood by the peptides of the invention enable amplification in vitro of the replication of the HIV virus and, thus, can promote its detection and its typing. Compositions comprising the peptides of the invention are, thus, also useful for the diagnosis of an infection by the HIV viruses.

With regard to treatment of an HIV infection, the efficacy of antiviral agents is reinforced by administering them prior to or simultaneously with one or more peptides of the invention. In fact, the peptides of the invention promote the replication and liberation of HIV viruses in vivo, especially residual HIV viruses which remain present in the organism after antiviral treatment. Administration of the peptides according to the invention, by activating these viruses, makes them more accessible to the antiviral agents and, thus, more easily destructible.

It is, moreover, known that, besides IL-2, the cytokines generally play a role in cellular proliferation, more particularly, in the case of blood cells. We, therefore, attempted to demonstrate the role of HARP and of pAHA in the expression of cytokines. Thus, was demonstrated the inductive properties of the expression of the cytokines of inflammation. The term "cytokines of inflammation" is understood to mean preferentially TNF-alpha, IL-1, IL-6 and INF-gamma.

We tested the induction of expression of three cytokines of inflammation (TNF-alpha, IL-1 and IL-6) by PBMC cells treated by HARP, and the induction of the expression of IL-6 by two pAHA peptides according to the invention, the sequences of which are presented in Example 5 below. The results obtained with the HARP molecule indicate that HARP is capable of inducing in a dose-dependent manner the expression of the cytokines TNF-alpha, IL-1 and IL-6.

The results obtained with both pAHA peptides show that they are capable of stimulating the expression of IL-6. An increase in the expression of these cytokines was also detected after addition to the cells of other peptides according to the invention, stemming from angiogenin and the tat protein (see Table I). No expression of the inflammatory cytokines was detected when the HARP molecule was denatured.

These results show that HARP and pAHA have in vitro and in vivo the capacity to stimulate by more than 100 times the production of cytokines of inflammation. The invention consequently pertains most particularly to a pharmaceutical composition comprising one or more pAHA peptides, and possibly another compound, that is useful for stimulating production of cytokines of inflammation. Such a composition according to the invention is, thus, particularly indicated in the prevention or treatment of diseases linked to immunodepression.

These studies showed that the tissues treated with HARP or pAHA present a very large number of mononucleated cells thereby promoting muscle regeneration. These results, combined with the two previously described results concerning the effect of the pAHA peptides on cell and tissue regeneration, demonstrate the effect of HARP and pAHA on tissue regeneration and, more particularly, on muscle tissues.

These results justify the use of the peptides of the invention or a composition containing them for promoting growth and differentiation of cells in cultures, especially lymphoid cells, such as endothelial cells and T lymphocytes. In fact, the culture of these cells is often performed in the context of diagnostic tests.

As indicated previously, the peptides of the invention can be produced by genetic expression of a polynucleotide sequence coding said peptides. The invention also provides a nucleic acid molecule constituted by or comprising at least one polynucleotide sequence coding for a peptide as defined previously. Such nucleic acid molecules are more particularly vectors, such as plasmids which can be used for transforming host cells in vitro or in vivo. The term "host cells" is understood to mean, for example, bacteria allowing production of the peptides of the invention. Also included are mammal cells, more particularly, human cells useful for cellular or genetic therapy methods applied to the previously described pathologies for which the peptides of the invention are useful. The invention, thus, provides compositions comprising as active principle at least one nucleic acid molecule or the cells described above.

EXAMPLE 1

Effect of HARP Protein on the Proliferation of Human Mononucleated Cells Derived from Peripheral Blood Human mononucleated cells originating from different healthy donors were isolated from peripheral blood after centrifugation on a Ficoll-Hypaque pad (Pharmacia Biotech) in accordance with the manufacturer's instructions. The cells were washed then cultured in RPMI 1640 medium supplemented by 10% heat-inactivated fetal calf serum (56° C., 30 min), 100 units/ml of penicillin and 100 µg/ml of streptomycin. The cells were inoculated at the rate of $10^6$ cells per ml in a 96-well (round bottoms) culture plate (Costar). They were cultured for 7 days in the presence or not of human recombinant HARP protein produced in $E.$ $coli$ at the concentration of 100 ng/ml. In the last 18 hours of culture, 1 µCi of tritiated thymidine was added to each of the wells. The radioactivity incorporated in the cell nuclei was then measured using a scintillation counter. The results obtained are shown in FIG. 1.

Analysis of these results showed us that the HARP polypeptide is capable of stimulating the incorporation of tritiated thymidine in the nucleus of PBMCs. Depending on the donor, it should be noted that the index of stimulation (defined as the ratio of radioactivity incorporated in the cells treated by HARP to that in the control cells not treated by HARP) varied from 2.3 to 51.7 times (cf. the results of experiments no. 4 and no. 7). This diversity of response can suggest that there exists a relation between the response of the cells to HARP and the activation state of the immune system of the tested individual. The histogram shown as an insert in FIG. 1 shows that treatment with 100 ng/ml of HARP induces an increase in the number of cells of 2.9 times in relation to the untreated control, demonstrating that the incorporation of thymidine observed is clearly proportional to the number of cells. This cell counting was performed with the cells used for the incorporation of tritiated thymidine in experiment no. 7.

The dose-response curve of HARP protein (0.1 to 500 ng/ml) tested on PBMCs is shown in FIG. 2A.

Analysis of this curve shows us that a maximum effect is attained for a HARP concentration of 1 ng/ml of culture medium inducing a stimulation of DNA incorporation of 4.5 to 7.5 times in relation to a control culture without addition of HARP. It should be noted that there is a decrease in the radioactivity incorporated for the higher doses of HARP ranging from 1 to 500 ng/ml. No stimulation was seen when using the midkine protein (MK), a protein that exhibits 50% homology in amino acids with HARP, tested in a range of concentrations from 0.1 to 500 ng/ml. Positive stimulation controls were implemented using phytohemagglutinin (PHA) 2.5 µg/ml and tetanus toxin (TT) 1800 IU/ml (FIG. 2B). No stimulation was seen after the addition of IL-2, thereby demonstrating an absence of activation of the cells used for these tests.

EXAMPLE 2

Role of HARP Protein as Co-stimulator of the Specific Immune Response

Activation of the T lymphocytes can be obtained via the activator of the antigen receptor (TCR) associated with the major histocompatibility complex (MHC). In addition to specific TCR-MHC/antigen recognition, this system furthermore requires the action of adhesion molecules playing a role of co-activation and amplification of the response. Following these data, we investigated whether HARP could amplify cellular proliferation either by stimulation of the T lymphocyte receptor by means of an anti-CD3 or by a memory antigen, tetanus toxin.

a) Effect of HARP Protein on the Stimulation Induced by the T Lymphocyte Receptor.

Activation of the T lymphocyte receptor was attained by treating the lymphocytes with an anti-CD3 monoclonal antibody (1/100, Immunotech). The effect of HARP on the cellular proliferation of PBMCs was tested by adding an optimal concentration of HARP (1 ng/ml, cf. Example 1) in the presence or lack thereof of anti-CD3. The cultures as well as the quantification of the incorporated tritiated thymidine were implemented as described in Example 1. The results obtained are presented in FIG. 3.

In the absence of HARP, the anti-CD3 antibody (1/100) stimulates, after 7 days of incubation with the cells, the incorporation of tritiated thymidine by 25 times (control: 600±60 cpm; anti-CD3: 15,000±200 cpm). At the dose of 1 ng/ml of HARP and in the absence of anti-CD3, there was seen for this donor an amplification of 5.8 times in relation to the control (control: 600 cpm; HARP: 3500±cpm). At this same dose of HARP, an amplification of 33 times in the response was seen when the cells were co-stimulated with HARP/anti-CD3 (control: 600±cpm; HARP/anti-CD3: 20,000±cpm). This result shows us that the HARP protein exerts an additive co-stimulation action on the lymphocytes by which TCR is activated. At higher HARP concentrations (10 and 100 ng/ml) and in the presence of anti-CD3, a weaker and a very low incorporation of thymidine were seen.

We observed in these cultures a very high cellular mortality which was not seen when HARP was used alone at the same doses. These results show that HARP has a dose-dependent co-stimulator effect on the immune response associated with T lymphocytes.

b) Effect of HARP Protein on the Stimulation Induced by a Memory Antigen.

PBMC cells cultured under the conditions described above were stimulated by tetanus toxin (1800 IU/ml, Merieux) alone or in association with HARP protein used at a concentration ranging from 0.1 to 100 ng/ml. The tetanus toxin specifically amplifies a subpopulation of memory T lymphocytes.

Addition of tetanus toxin to PBMCs stimulates, after 7 days of incubation, the incorporation of tritiated thymidine by 71 times (control: 600±60 cpm; tetanus toxin: 43,000±500 cpm), whereas a stimulation of 5.8 times in relation to the unstimulated control is seen with HARP at 1 ng/ml (control: 600±60 cpm; HARP: 3500±200 com). Stimulation of the incorporation of tritiated thymidine of 108 times in relation to the control is seen when the cells are co-stimulated by HARP at the dose of 1 ng/ml and tetanus toxin (control: 600±60 cpm; HARP/tetanus toxin: 65,000±700 cpm). The results presented in FIG. 2 show us a synergy of action on the stimulation of PBMCs between a memory antigen and HARP.

EXAMPLE 3

Determination of the Amplified Cell Population After Treatment by HARP in a PBMC Culture The cells were isolated from peripheral blood of normal subjects (blood donors) and collected in a Vacutainer tube containing EDTA. Mononucleated cells were separated by ficoll gradient, counted and adjusted to $10^6$ per ml. The cells were incubated for 5 days at 37° C. in humid atmosphere with 5% $CO_2$ in the presence of HARP or other peptides at concentrations which are mentioned in each of the Examples described.

Table II presents the effects of the HARP molecule tested at a concentration of 1 µg/ml on the proliferation of lymphoid cells.

TABLE II

| Antibody | Control % | HARP % | Variation (%) |
|---|---|---|---|
| CCD19 | 2 | 4 | — |
| CCD2 | 92 | 95 | — |
| CCD4 | 47 | 68 | +45 |
| CCD8 | 33 | 22 | — |
| CCD16/56 | 17 | 18 | — |
| CCD25 | 12 | 47 | — |
| CCD45RA | 58 | 34 | — |
| CCD45RO | 30 | 64 | +113 |
| RA/RO | 1.9 | 0.5 | — |
| CCD4+ CD45RA+ | 22 | 15 | −31 |
| CCD4+ CD45RO+ | 21 | 49 | +133 |
| RA/RO | 1 | 0.3 | — |

The analysis of the results presented in this test showed us that after treatment of a PBMC culture with HARP, one finds a strong enrichment to the degree of about 45% of the CD4+ lymphocyte population. A strong CD45RO augmentation was also observed (+113%), corresponding to an augmentation of the CD4+/CD45RO+ memory CD4 (+133%). These results indicate that one observes an amplification of CD4+ lymphocytes expressing the CD45RO characteristic of memory T lymphocytes. This Example illustrates the adjuvant role of HARP in the immune response, notably by amplification and co-activation of the CD45RO lymphocyte subpopulation.

EXAMPLE 4

Figure 4:
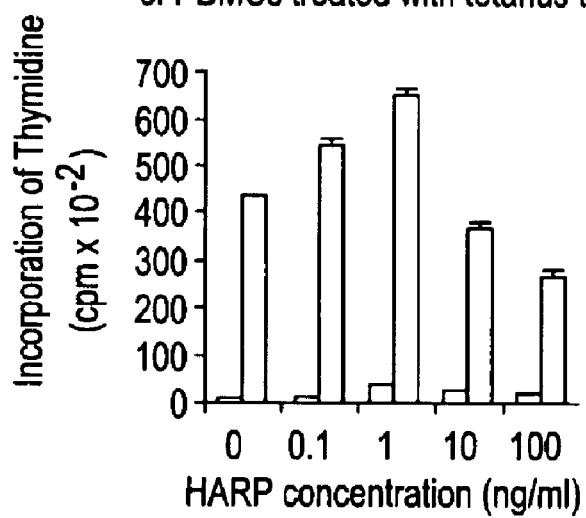
FIG. 4 shows the dose-response effect of HARP on PBMCs treated by tetanus toxin. The cells were cultured as described above. It should be noted that a high cell mortality was seen when the cells were treated with 100 ng/ml of HARP in the presence of tetanus toxin (800 IU/mi). Hatched bar: HARP alone; clear bar: HARP+tetanus toxin.
Figure 5:
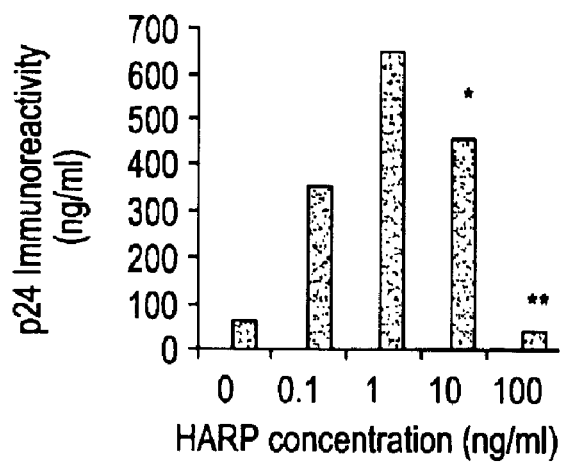
FIG. 5 shows the effect of the HARP protein on the replication of HIV by measurement of the p24 immunoreactivity. PBMCs obtained from an HIV-infected patient were incubated according to the protocol described in example 4 for 3 days with variable concentrations of HARP (0.1–100 ng/ml). Viral replication was assessed by measurement of the immunoreactivity associated with the p24 protein present in the culture medium. (*) low cell mortality; (**) high cell mortality. Production of the virus was evaluated by the "Abbott HIV Ag monoclonal" test which is a quantitative immunoenzymatic solid-phase determination test of the sandwich type. The viruses present in the sample to be tested were lysed by Triton X100 then the lysate was incubated with polystyrene beads covered with anti-p24 monoclonal antibody. After incubation, the beads were washed and the presence of specific immunoglobulins was visualized with a second anti-Ig mouse antibody bound to peroxidase. Visualization was then performed by adding a substrate of the peroxidase: ortho-phenylenediamine.

Action of the HARP Molecule on Mononucleated Cells Obtained from the Peripheral Blood of HIV-infected Subjects Activation of the T lymphocytes and monocytes by cytokines induces production and/or activation of the nuclear factors of the host cell capable of reactivating viral transcription. This viral reactivation induced by IL-1 and TNF-α is dependent in part on the activation of the NF-κB factor. During infection by HIV, secretion by circulating monocytes of the cytokines IL-1, Il-6 and especially TNF-α, which are capable of inducing or augmenting the replication of HIV in the T lymphocytes/monocytes, suggests that these cytokines can augment the progression of the disease. The results in FIG. 5 indicate that PBMCs obtained from an AIDS patient (CD4<200/mm$^3$) activated solely by HARP protein are capable of producing the HIV virus as measured by the production of the viral antigen p24. This production is maximal for a concentration of HARP of 1 ng/ml. For a concentration of 100 ng/ml, noteworthy cell death is seen. Thus, based on this Example, it is possible to suggest, on the one hand, that HARP can enable amplification in vitro of the expression of P24 and be used for the typing of HIV viral strains and, on the other hand, in vivo as 1) inducer of the replication of the virus, thereby facilitating the action of antiviral agents on the quiescent infected lymphocytes or 2) at high doses (corresponding to the effects observed in vitro at 100 ng/ml) induce the death of chronically activated T cells (see the preceding Examples illustrated by FIGS. 3 and 4).

EXAMPLE 5

Activation of Lymphocytes by HARP Peptides

Following the protocol described in Example 1, we tested the capacity of two peptides, whose sequences correspond to the terminal NH$_2$ part and terminal COOH part of HARP, to induce cellular multiplication of PBMCs. The sequences of these peptides are as follows:

NH2-AEAGKKEKPEKKVKKSDCGEW-COOH; 21 amino acids.
(SEQ ID NO: 21) Peptide 1

NH2-AESKKKKKEGKKQEKMLD-COOH; 18 amino acids.
(SEQ ID NO: 22) Peptide 2

Figure 6:
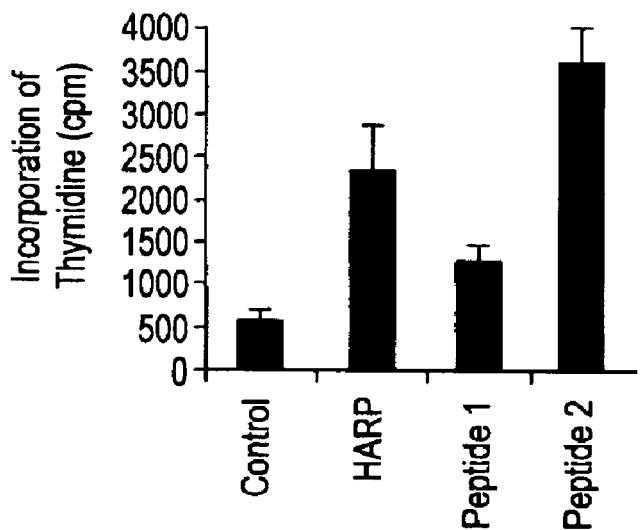
FIG. 6 shows the activation of the mononucleated cells of the peripheral blood by HARP peptides. The PBMCs were cultured for 7 days in RPMI culture medium containing 10% fetal calf serum in the absence of or in the presence of 1 ng/ml HARP protein or 1 µg/ml of peptides 1 or 2. The incorporation of tritiated thymidine was determined as described above.

The results are presented in FIG. 6 and show that compared to the HARP protein, peptide 2 is capable of inducing an activation response of PBMCs better than HARP, close to two times higher. For comparable concentrations, peptide 1 has a weaker effect, close to half that of HARP, but clearly superior to the control (more than two times higher).

EXAMPLE 6

Induction of the Expression of TNF-α, IL-6 and IL-1 by PBMCs Treated by HARP The cells were isolated from peripheral blood of normal subjects (blood donors) and collected in a Vacutainer tube containing EDTA. Mononucleated cells were separated by ficoll gradient, counted and adjusted to 10$^6$ per ml. The cells were incubated for 3 or 7 days at 37° C. in humid atmosphere with 5% CO$_2$ in the presence of variable concentrations of HARP ranging from 1 to 1000 ng/ml or other peptides which are mentioned in the legends of the figures.

Figure 7:
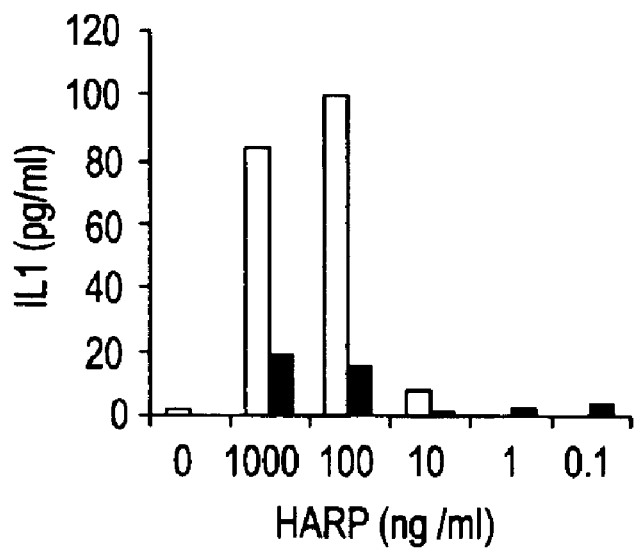
FIG. 7 shows the study of the effect of HARP on the expression of IL-1 after 3 days (clear bars) or 7 days (solid bars) of culture. Quantitative determination of these cytokines was performed using an ELISA test from R&D.
Figure 8:
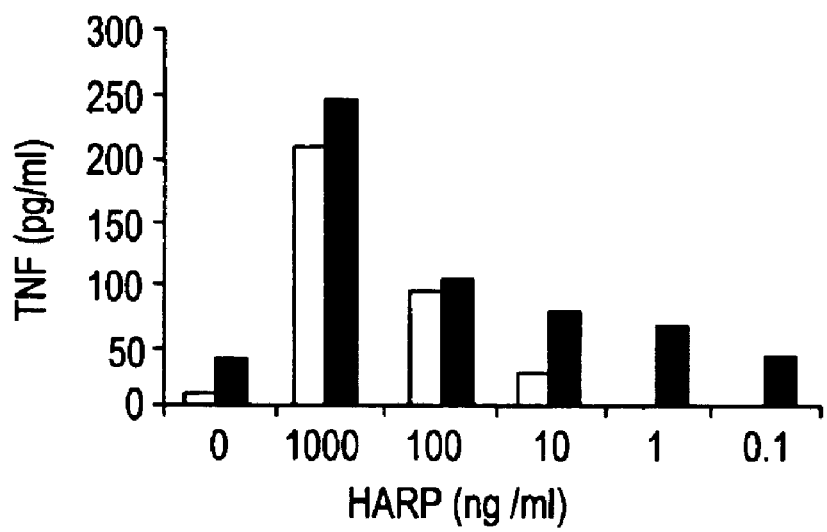
FIG. 8 shows the effect of HARP on the expression of TNF-α after 3 days (clear bars) or 7 days (solid bars) of culture. Quantitative determination of these cytokines was performed using an ELISA test from R&D.
Figure 9:
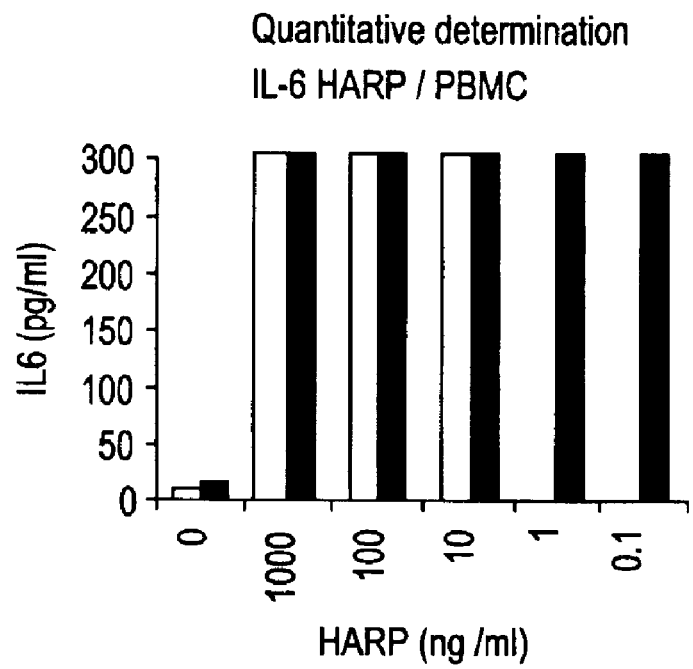
FIG. 9 shows the effect of HARP on the expression of IL-6 after 3 days (clear bars) or 7 days (solid bars) of culture. Quantitative determination of these cytokines was performed using an ELISA test from R&D.
Figure 10:
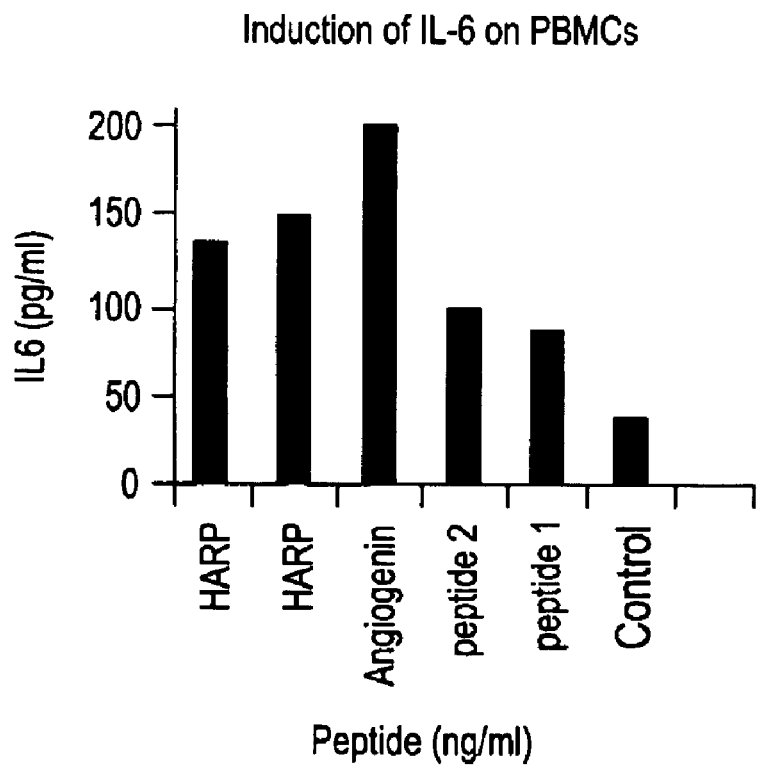
FIG. 10 shows the expression of IL-6 by peptides 1 and 2 corresponding to the $NH_2$ and COOH parts of the HARP polypeptide. Quantitative determination of these cytokines was performed after 7 days of incubation using an ELISA test from R&D.

The results are shown in FIGS. 7, 8 and 9. Analysis of these results shows that the HARP molecule is capable of inducing in a dose-dependent manner the expression of the cytokines IL-1β (FIG. 7), TNF-α (FIG. 8) and IL-6 (FIG. 9).

This Example shows that peptides 1 and 2, whose structures are presented in Example 5, are capable of stimulating the expression of IL-6. Augmentation of the expression of these cytokines is also detected after addition to the cells of tat peptides or other molecules (angiogenin, tat protein; result not shown) presenting a homologous protein domain. No expression of these inflammatory cytokines is detected in this system when the HARP molecule is denatured or when the cells are treated with LPS.

EXAMPLE 7

Effect of HARP Peptides in Muscle Regeneration

The effect of peptides 1 and 2, whose structures are defined in Example 5, on muscle regeneration was tested following the protocol presented below and following the technique described in the publication by Bassaglia et al. (Y. Bassaglia and J. Gautron (1995): Fast and slow rat muscle degenerate and regenerate different after whole crush injury; J. Muscle Res. Cell Motil. 16, 420–429). After the rat is anesthetized (Wistar rat aged 2 to 3 months), the soleus muscle is denervated and then crushed with flat-end forceps. The sample to be tested is then injected with a volume of 50 µl of PBS. After four days of treatment, the animals are sacrificed, the muscles are collected then frozen in liquid nitrogen. Sections 8-µm thick are prepared using the cryostat and then stained with Masson's trichrome stain.

Figure 11C:
FIG. 11C shows soleus muscle treated by peptide 2 (50 µl, 1 µl).
Figure 11B:
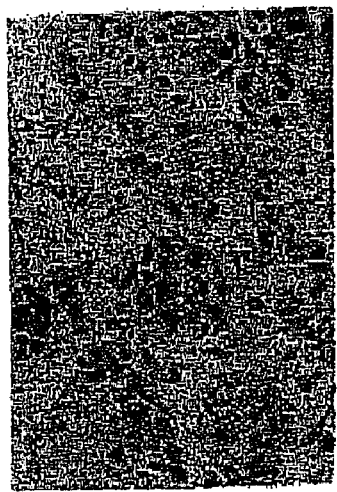
FIG. 11B shows soleus muscle treated by peptide 1 (50 µl, 1 µl).
Figure 11A:
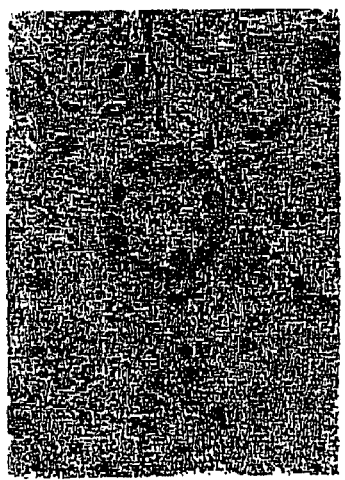
FIG. 11A shows soleus muscle treated by PBS (50 µl).

The results are presented in FIG. 11. Analysis of these sections indicates that the muscle treated with 1 µg of peptide 1 presents a number of mononucleated cells (FIG. 11.2) much higher than the muscles treated with peptide 2 (FIG. 11.3) or solely with 50 µl of PBS (FIG. 11.1). This observation indicates that the injection of peptide 1 into a crushed muscle induces, after 4 days of treatment, an augmentation in the number of mononucleated cells present in the endomysial tubes promoting tissue regeneration.

EXAMPLE 8

Effect of HARP Peptides on Angiogenesis

The chicken allantoic membrane test (CAM test) was used in this study to evaluate in vivo the effect of HARP peptides 1 and 2 on the induction of angiogenesis. The structures of these peptides were presented in Example 5. The experimental procedure was the following:

Fertilized chicken eggs were incubated at 37° C. for 3 days. After this incubation period, two openings were made in the shell and 3 to 4 ml of albumin was aspirated with a syringe. The samples to be tested were deposited on disks of methyl cellulose 3 mm in diameter. After drying, each disk was deposited on day 4 in one of the openings in a shell. Observation was carried out after a period ranging from 9 to 13 days. Each quantitative determination point was implemented 10 times and each determination was repeated 3 times. The overall results are presented in Table 3 below.

TABLE III

| Sample | FGF-2 (100 ng) | Control | HARP (1.5 µg) | Peptide 1 (1.5 µg) | Peptide 2 (1.5 µg) |
|---|---|---|---|---|---|
| Response | ++++ | +/− | ++ | ++ | −− |

Figure 12B:
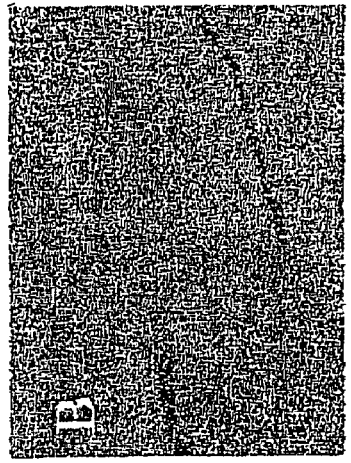
FIG. 12B shows control treated with PBS.
Figure 12A:
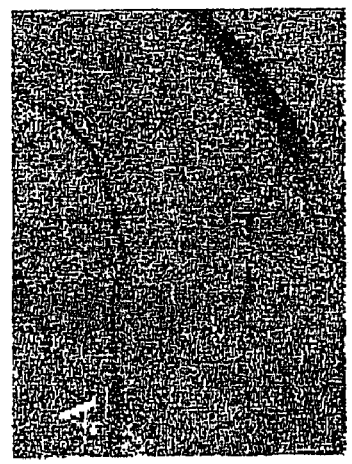
FIG. 12A shows treatment with peptide 1.

The effect of peptide 1 on the induction of angiogenesis in the CAM test is illustrated in the next Example (FIG. 12).

EXAMPLE 9

Expression and Determination of the Mitogenic Activity of the Peptide Corresponding to the N Terminal Part of the HARP Molecule (Residues 1 to 14).

The N terminal peptide (amino acids 1–14) of human HARP was obtained by recombination in a eukaryote expression system.

This peptide was obtained from the cDNA of subcloned EcoRI human HARP in the eukaryote expression vector PcDNA-3 (InVitroGen) by creation of a stop codon at the level of amino acid number 15 (QuickChange Directed Mutagenesis Kit, Stratagene, USS).

Figure 13:
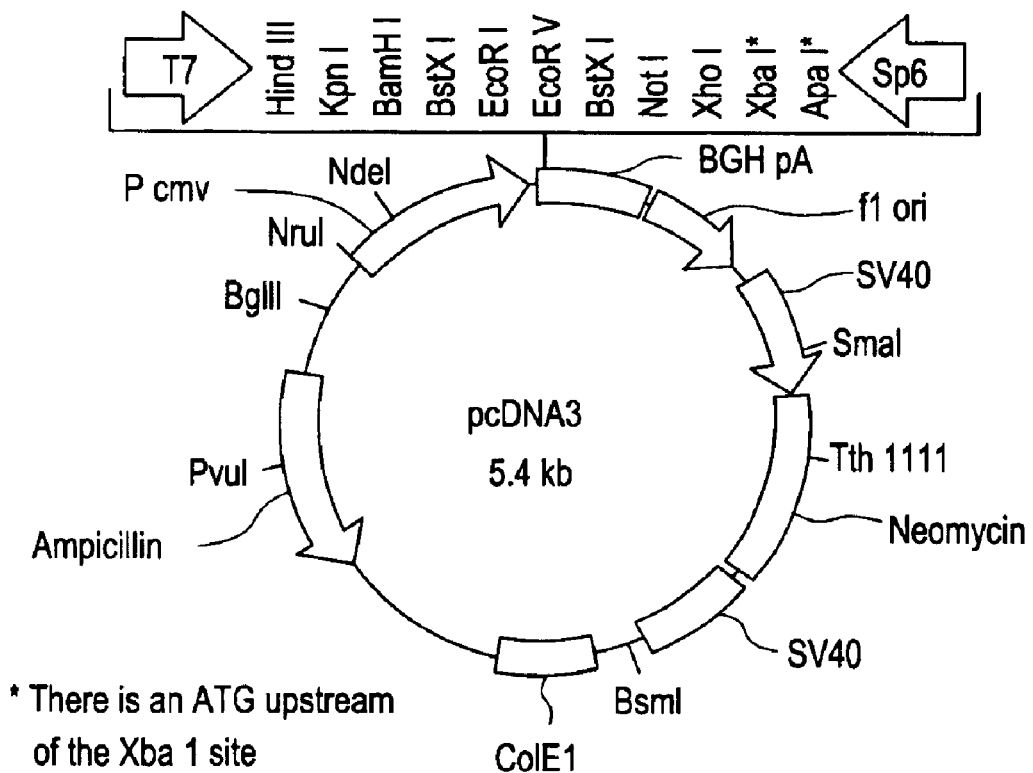
FIG. 13 is a schematic representation of the plasmid used for producing the peptide corresponding to the N terminal part (residues 1 to 14) of HARP.

A schematic representation of the plasmid employed is given in FIG. 13.

After verification of the generated mutation by sequencing, eukaryote cells (NIH 3T3) were transfected with this construction (Fungene, Roche, N.J., USA). The expression was monitored by Western blot from culture media conditioned by the transfected cells using anti-N-terminal HARP antibody (residues 1–15, commercialized by Santa Cruz, Calif., USA). The cells were cultured for 72 h in the presence of butyrate and then the conditioned medium was recovered. After purification of the peptide by means of cationic chromatography and a reverse phase (Waters, Symmetry®, C18, 5 µm, 4.6×250 mm). Elution of the column was performed by a linear gradient of acetonitrile. The presence of peptide in the eluted fractions was monitored by measuring the optical density at 220 nm. Quantitative determination of the mitogenic activity induced by the peptide purified in this manner was performed according to the following protocol:

The cells used were HUVEC cells (Clonetics) used between passages 1 to 5. Each of the wells of a 48-well culture plate (Costar) was incubated for 1 night at 4° C. with a solution of HARP (100 ng/ml), of purified HARP peptide (100 ng/ml) or solely the negative control buffer. After rinsing the wells with a PBS solution, the cells were inoculated at the rate of $2 \times 10^4$ cells per $cm^2$ in the DMEM culture medium containing 2% of fetal calf serum. Each quantitative determination was performed in triplicate.

Induction of cellular proliferation was assessed by counting the cells after 72 hours of culture.

The results are presented in Table IV below and indicate that the HARP peptide corresponding to the N terminal part of HARP and produced by genetic engineering induced cellular proliferation of the endothelial cells.

TABLE IV

| Sample tested | Number of cells |
|---|---|
| HARP | 129,000 ± 26,000 |
| Control | 30,000 ± 8100 |
| HARP peptide | 12,000 ± 14,000 |

BIBLIOGRAPHIC REFERENCES

1. Bohlen P. and Kovesdi I., 1991. HBNF and MK, members of a novel gene family of heparin-binding proteins with potential roles in embryogenesis and brain function. Prog. Growth Factor Res. 3:43.
2. Laaroubi K., Vacherot F., Delbe J., Caruelle D., Barritault D. and Courty J., 1995. Biochemical and mitogenic properties of the heparin-binding growth factor HARP. Prog. Growth Factor Res. 6:25.
3. Rauvala H., 1989. An 18-kd heparin-binding protein of developing brain that is distinct from fibroblast growth factors. EMBO J. 8:2933.
4. Merenmies J. and Rauvala H., 1990. Molecular cloning of the 18-kDa growth associated protein of developing brain. J. Biol. Chem. 265:16721.
5. Hampton B. S., Marshak D. R. and Burgess W. H., 1992. Structural and functional characterization of full-length heparin-binding growth associated molecule. Mol. Biol. Cell. 3:85.
6. Milner P. G., Li Y. S., Hoffman R. M., Kodner C. M., Siegel N. R. and Deuel T. F., 1989. A novel 17 kD heparin-binding growth factor (HBGF-8) in bovine uterus: purification and N terminal amino acid sequence. Biochem. Biophys. Res. Commun. 165:1096.
7. Neame P. J., Young C. N., Brock C. W., Treep J. T., Ganey T. M., Sasse J. and Rosenberg L. C., 1993. Pleiotrophin is an abundant protein in dissociative extracts of bovine fetal epiphyseal cartilage and nasal cartilage from newborns. J. Orthop. Res. 11:479.
8. Gieffers C., Engelhardt W., Brenzel G., Matsuishi T. and Frey J., 1993. Receptor binding of osteoblast-specific factor I (OSF-I/HB-GAM) to human osteosarcoma cells promotes cell attachment. Eur. J. Cell. Biol. 62:352.
9. Fang W., Hartmann N., Chow D. T., Riegel A. T. and Wellstein A., 1992. Pleiotrophin stimulates fibroblasts and endothelial and epithelial cells and is expressed in human cancer. J. Biol. Chem. 267:25889.
10. Szabat E. and Rauvala H., 1996. Role of HB-GAM (heparin-binding growth-associated molecule) in proliferation arrest in cells of the developing rat limb and its expression in the differentiating neuromuscular system. Dev. Biol. 178:77.
11. Wellstein A. et al., 1992. A heparin-binding growth factor secreted from breast cancer cells homologous to a developmentally regulated cytokine. J. Biol. Chem. 267:2582.
12. Laaroubi K., Delbe J., Vacherot F., Desgranges P., Tardieu M., Jaye M., Barritault D. and Courty J., 1994. Mitogenic and in vitro angiogenic activity of human recombinant heparin affin regulatory peptide. Growth Factors 10:89.
13. Peng H. B., Ali A. A., Dai Z., Daggett D. F., Raulo E. and Rauvala H., 1995. The role of heparin-binding growth-associated molecule (HB-GAM) in the postsynaptic induction in cultured muscle cells. J. Neurosci. 15:3027.
14. Mitsiadis T. A., Salmivirta J., Muramatsu T., Muramatsu H., Rauvala H., Lehtonen E., Jalkanen M. and Thesleff I., 1995. Expression of the heparin-binding cytokines, midkine (MK) and HB-GAM (pleiotrophin) is associated with epithelial-mesenchymal interactions during fetal development and organogenesis. Development 121:37.
15. Vandervinden J. M., Mailleux P., Schiffmann S. N. and Vanderhaeghen J. J., 1992. mRNA in developing cellular distribution of the new growth factor peliotrophin (HB-GAM) and adult rat tissues. Anat. Ernbryol. 186:387.
16. Ledoux D., Caruelle D., Sabourin C., Liu J., Crepin M., Barritault D. and Courty J., 1997. Cellular distribution of the angiogenic factor heparin affin regulatory peptide (HARP) mRNA and protein in the human mammary gland. J. Histochem. Cytochem. 45:1.
17. Seddon A. P., Hulnes J. D., Decker M. M., Kovesdi I., Fairhurst J. L., Backer J., Dougher-Vermazen J. and Bohlen P., 1994. Refolding and characterization of human recombinant heparin-binding neurite-promoting factor. Protein expr. Purif. 5:14.
18. Smith P. et al., 1985. Measurement of protein using bicichoninic acid. Anal. Biochem. 150:543.
19. Nvotny W. F., Maffi T., Mehta R. L. and Milner P. G., 1993. Identification of novel heparin-releasable proteins, as well as the cytokines midkine and peliotrophin, in human postheparin plasma. Arterioscler. Thromb. 13:1798.
20. Kuo M. D., Huang J. S. and Huang J. S., 1992. Characterization of heparin-binding growth-associated factor receptor on NIH 3T3 cells. Biochem. Biophys. Res. Commun. 182:188.
21. Raulo E., Chernousov M. A., Carey D. J., Nolo R. and Rauvala H., 1994. Isolation of a neuronal cell surface receptor pf heparin binding growth-associated molecule (HB-GAM). Identification as N-syndecan (syndecan-3). J. Biol. Chem. 269:12999.
22. Maeda N., Nishiwaki T., Shintani T., Hamanaka H. And Noda M., 1996. 6B4 proteoglycan/phosphacan, an extracellular variant of receptor-like protein-tyrosine phosphatase zeta/RPTPbeta, binds pleiotrophin/heparin-binding growth-associated molecule (HB-GAM). J. Biol. Chem. 271:21446.

23. Kretschmer P. J., Fairhurst J. L., Decker M. M., Chan C. P., Gluzman Y., Bohlen P. and Kovesdi I., 1991. Cloning, characterization and developmental regulation of two members of a novel human gene family of neurite outgrouwth-promoting proteins; Grouwth factors. 5:99.

24. Ratovitski E. and Burrow C. R., 1997. Midkine stimulates Wilms' tumor cell proliferation via signaling receptor. Cell. Mol. Biol. 43:425.

25. Ratovitski E., Kotzbauer T., Milbrandt J., Lowenstein C. J. and Burrow C. R., 1998. Midkine induces tumor cell proliferation and binds to a hight affinity signaling receptor associated with JAK tyrosine kinases. J. Biol. Chem. 273:3654.

What is claimed is:

1. A method of stimulating production of cytokine of inflammation IL-6 comprising administering a therapeutically effective amount of a pharmaceutical composition comprising:

a peptide corresponding to formula (II) below:

$(A)_n$-Lys-Lys-Glu-Lys-Pro-Glu-Lys-$(A)_m$   (SEQ ID NO: 14)

in which:

A is any amino acid;

n and m are each whole numbers from 0 to 20 whose sum n+m is between 0 and 20; and a pharmaceutically acceptable carrier.

2. The method according to claim 1, wherein pharmaceutical composition comprises the a peptide of SEQ. ID. No. 21.

* * * * *